United States Patent [19]

Heidenreich et al.

[11] Patent Number: 4,786,729
[45] Date of Patent: Nov. 22, 1988

[54] BENZIMIDAZOLO-QUINAZOLINES

[75] Inventors: Holger Heidenreich, Cologne; Gert Jabs, Odenthal, both of Fed. Rep. of Germany

[73] Assignee: Bayer Aktiengesellschaft, Leverkusen, Fed. Rep. of Germany

[21] Appl. No.: 34,810

[22] Filed: Apr. 3, 1987

[30] Foreign Application Priority Data

Apr. 12, 1986 [DE] Fed. Rep. of Germany ....... 3612440

[51] Int. Cl.$^4$ .................... C09B 57/00; C07D 487/04
[52] U.S. Cl. .................... 544/125; 503/223; 544/105; 544/230; 544/247
[58] Field of Search ................ 544/105, 125, 247, 230

[56] References Cited

U.S. PATENT DOCUMENTS 4,465,833  8/1984  Lau et al. .................... 544/247 X
4,695,633  9/1987  Berneth et al. ................ 544/247 X

OTHER PUBLICATIONS

Rao, et al., Indian J. Chemistry, vol. 15B, pp. 1100–1102 (12/77).
Davis, et al., Chemical Abstracts, vol. 57:811a–812i (1962).
Zaika, et al., Chemical Abstracts, vol. 65:15376f–15377a (1966).
Korshak, et al., Chemical Abstracts, vol. 88:152537k (1978).
Korshak, et al., Chemical Abstracts, vol. 90:105507g (1979).
Pandey, et al., Acta Pharm Jugosl. 1986, 36(3) pp. 281–287, abstract only supplied, CA: 106: 169230t (1987).
Pandey, et al., Chemical Abstracts, vol. 104:50842n (1986).
Vostrova, et al., Chemical Abstracts, vol. 106:32976w (1987).

Primary Examiner—Donald G. Daus
Assistant Examiner—Diana G. Rivers
Attorney, Agent, or Firm—Sprung Horn Kramer & Woods

[57] ABSTRACT

Benzimidazolo-quinazolines of the general formula

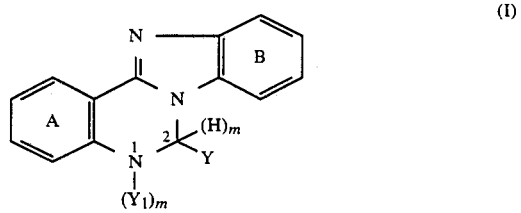

in which
Y denotes a radical of the formula

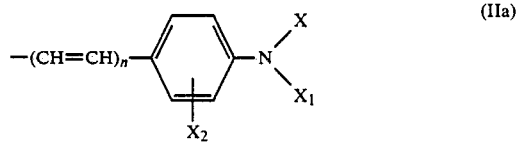

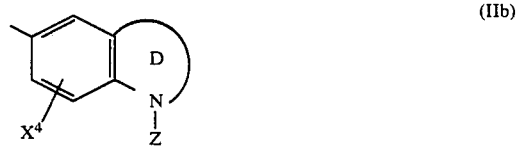

or

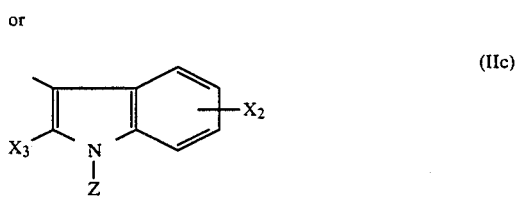

$Y_1$ denotes hydrogen or alkyl,
X and $X_1$, independently of one another, denote hydrogen, alkyl, cycloalkyl, aryl or aralkyl, or
X and $X_1$, together with the nitrogen atom connecting them, denote a 5- or 6-membered ring,
$X_2$ denotes hydrogen, halogen, alkyl, alkoxy or alkoxycarbonyl,
$X_3$ denotes hydrogen, alkyl or aryl,
$X_4$ denotes hydrogen, cyano, halogen, alkyl or alkoxy,
Z denotes hydrogen, alkyl, cycloalkyl or aralkyl,
D denotes an optionally hydrogenated 5- or 6-membered ring, and
m and n, independently of one another, denote 0 or 1,
in which a double bond is in the positions labelled with 1 and 2 when m=0 and a single bond is in these positions when m=1, and
in which the rings A, B and D are the radicals X, $X_1$, $X_2$, $X_3$, $X_4$ and Z may carry non-ionic substituents which are conventional in dyestuffs chemistry, are used as color formers in pressure- and heat-sensitive recording materials.

4 Claims, No Drawings

BENZIMIDAZOLO-QUINAZOLINES

The invention relates to benzimidazolo-quinazolines of the general formula

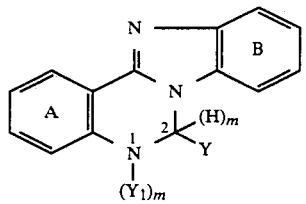

(I)

in which
Y denotes a radical of the formula

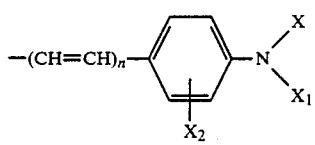 (IIa)

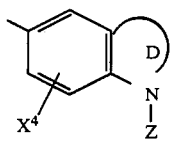 (IIb)

or

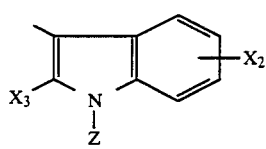 (IIc)

$Y_1$ denotes hydrogen or alkyl,

X and $X_1$, independently of one another, denote hydrogen, alkyl, cycloalkyl, aryl or aralkyl, or X and $X_1$, together with the nitrogen atom connecting them, denote a 5- or 6-membered ring, $X_2$ denotes hydrogen, halogen, alkyl, alkoxy or alkoxycarbonyl, $X_3$ denotes hydrogen, alkyl or aryl, $X_4$ denotes hydrogen, cyano, halogen, alkyl or alkoxy, Z denotes hydrogen, alkyl, cycloalkyl or aralkyl, D denotes an optionally hydrogenated 5- or 6-membered ring, and m and n, independently of one another, denote 0 or 1, sin which a double bond is located between the positions labelled with 1 and 2 when m=0 and a single bond is between these positions when m=1, and in which the rings A, B and D and the radicals X, $X_1$, $X_2$, $X_3$, $X_4$ and Z may carry the non-ionic substituents which are conventional in dyestuffs chemistry, processes for their preparation, and their use as colour formers in pressure- and heat-sensitive recording materials.

Non-ionic substituents which are conventional in dyestuffs chemistry are, for example: halogen, hydroxyl, alkoxy, aryloxy, aralkoxy, aryl, cycloalkyl, hetaryl, alkylmercapto, arylmercapto, aralkylmercapto, alkylsulphonyl, cyano, alkylcarbonyl, alkylcarbonyloxy, carbamoyl, alkoxycarbonyl, amino which may be substituted by 1 or 2 alkyl, aryl or aralkyl groups, acylamino, alkenyloxy, alkylcarbonyloxy and arylcarbonyloxy, and, as ring substituents, in addition alkyl, aralkyl, nitro, alkenyl or arylvinyl.

Alkyl preferably represents $C_1$-$C_{22}$-alkyl, particularly $C_1$-$C_{12}$-alkyl and very particularly $C_1$-$C_6$-alkyl, and alkenyl represents $C_2$-$C_5$-alkenyl.

Halogen is taken to mean, in particular, fluorine, chlorine and bromine.

In particular, cycloalkyl is taken to mean cyclopentyl and cyclohexyl, aryl is taken to mean phenyl and naphthyl, aralkyl is taken to mean benzyl and phenethyl, and hetaryl is taken to mean pyridyl, pyrimidyl, pyrazinyl, triazinyl, imidazolyl, oxazolyl, thiazolyl, triazolyl, thiadiazolyl or tetrazolyl. These radicals may themselves be substituted, for example, by $C_1$-$C_4$-alkyl, $C_1$-$C_4$-alkoxy, phenyl or halogen.

Amino groups whose substituents are cyclized, for example the $NXX_1$ group, preferably represent a 5- or 6-membered ring such as pyrrolidine, pyrazoline, piperidine, piperazine or morpholine, each of which may be substituted, for example, by $C_1$-$C_4$-alkyl or phenyl.

Acyl is preferably $C_1$- to $C_4$-alkylcarbonyl, $C_1$- to $C_4$-alkylsulphonyl, or benzoyl.

Together with the fused benzene ring, the ring D forms, for example, an indoline, tetrahydroquinoline or benzomorpholine radical. The benzene ring here is preferably unsubstituted and the heterocyclic ring is preferably substituted by $C_1$-$C_4$-alkyl.

Of the compounds (I), preferred benzimidazoloquinazolines are those of the formula

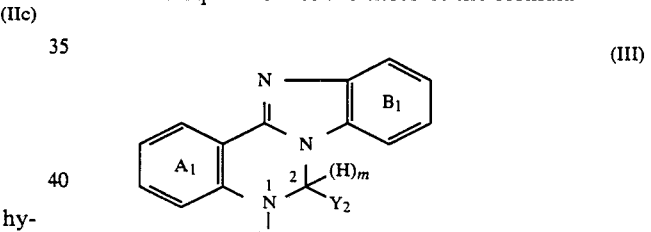 (III)

in which
$Y_2$ denotes a radical of the formula

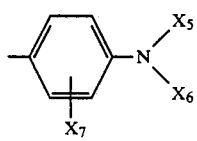 (IVa)

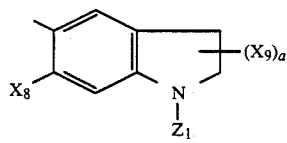 (IVb)

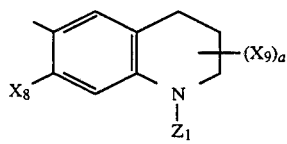 (IVc)

or

-continued

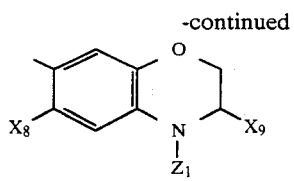 (IVd)

$Y_3$ denotes hydrogen or $C_1$-$C_4$-alkyl, $X_5$ and $X_6$, independently of one another, denote $C_1$-$C_6$-alkyl which may be substituted by halogen, $C_1$-$C_4$-alkoxy or cyano, cyclopentyl or cyclohexyl, each of which may be substituted by 1–4 $C_1$-$C_4$-alkyl groups, or denote phenyl, benzyl or phenethyl, each of which may be substituted by 1 or 2 $C_1$-$C_4$-alkyl, $C_1$-$C_4$-alkoxy, halogen, nitro, cyano or $C_1$-$C_4$-alkoxycarbonyl radicals, or $X_5$ and $X_6$, together with nitrogen atom connecting them, denote a pyrrolidine, piperidine or morpholine radical which may be substituted by $C_1$-$C_4$-alkyl, $X_7$ denotes hydrogen, halogen, $C_1$-$C_4$-alkyl, $C_1$-$C_4$-alkoxy or $C_1$-$C_4$-alkoxycarbonyl, $X_8$ denotes hydrogen, halogen, $C_1$-$C_4$-alkyl or $C_1$-$C_4$-alkoxy, $X_9$ denotes $C_1$-$C_4$-alkyl or phenyl, or 2 radicals $X_9$, which are both located on the same C atom, together denote trimethylene or tetramethylene, a denotes 0 or 1–4, and $Z_1$ denotes hydrogen, $C_1$-$C_8$-alkyl which may be substituted by halogen, cyano or $C_1$-$C_4$-alkoxy, benzyl or phenethyl, each of which may be substituted by halogen, $C_1$-$C_4$-alkyl or $C_1$-$C_4$-alkoxy, in which the rings $A_1$ and $B_1$ may be substituted by one or two radicals selected from cyano, halogen, $C_1$-$C_4$-alkyl, $C_1$-$C_4$-alkoxy, $NX_5X_6$, phenyl or benzyl, and m has the meaning specified in the case of (I).

Of the compounds (III), those to be emphasized are those of the formula

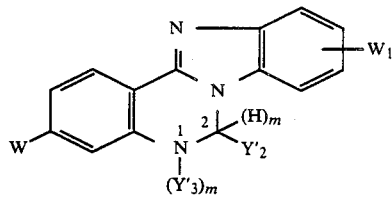 (V)

in which

W and $W_1$ denote hydrogen, chlorine, bromine, methyl or methoxy, $Y'_2$ denotes a radical of the formulae

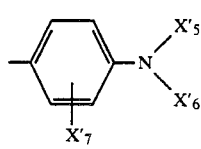 (VIa)

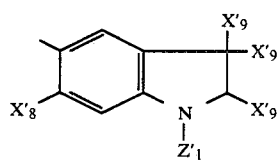 (VIb)

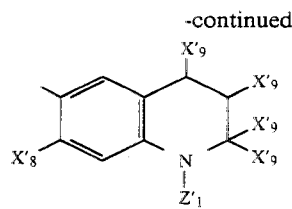 (VIc)

or

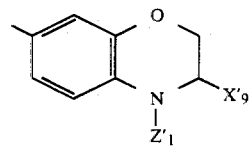 (VId)

$Y'_3$ denotes hydrogen or methyl, $X'_5$ and $X'_6$, independently of one another, denote $C_1$-$C_6$-alkyl or benzyl, or —N $X'_5$ $X'_6$ denotes piperidino, $X'_7$ denotes hydrogen, methyl, methoxy or ethoxy, $X'_8$ denotes hydrogen or methyl, $X'_9$ denotes hydrogen, methyl or ethyl, and $Z'_1$ denotes $C_1$-$C_8$-alkyl, β-cyanoethyl or benzyl, and m has the abovementioned meaning.

Of great importance are compounds of the formula

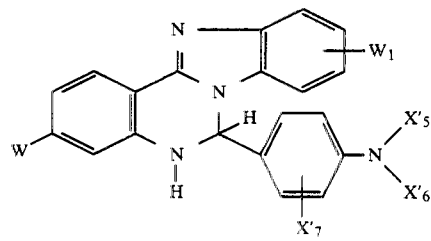 (VII)

and, above all, of the formula

(VIII)

in which the substituents have the abovementioned meaning.

The benzimidazolo-quinazolines, according to the invention, of the formula (I) are prepared by reaction of an aldehyde

Y—CHO (IX)

with a compound

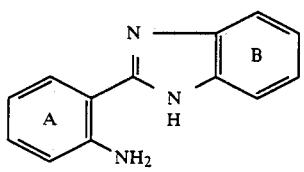 (X)

where A, B and Y have the abovementioned meaning, in a suitable solvent. A double bond between the indicated positions 1 and 2 may be obtained by subsequent oxidation.

Lower aliphatic alcohols, such as methanol, ethanol or isopropanol, or cyclic ethers, such as dioxane or tetrahydrofuran, or γ-butyrolactone, acetonitrile, dimethyl sulphoxide, dimethylformamide, dimethylacetamide, N-methylpyrrolidone or ethylene glycol monomethyl ether may be mentioned as suitable solvents.

The oxidation of the dihydro compound which is produced initially into the compound having the double bond in positions 1 and 2 of the formula (I) is carried out using oxidants, such as chromates, bichromates, chlorates, chlorites, peroxides, manganese dioxide, lead dioxide, chlorine, bromine, molecular oxygen, air, perborates, permanganates, hydrogen peroxide and, preferably, chloranil.

The reaction of the dihydro compound may be carried out at a temperature of 10° to 150° C., preferably between 20° and 80° C. The oxidation may be carried out, depending on the oxidant, between 10° and 150° C., preferably between 20° and 100° C.

The aldehydes (IX) are known from the literature (for example "Organikum, Organisch-Chemisches Grundpraktikum, Berlin 1970, P. 355 ff.). The compounds of the formula (V) can be obtained according to D.W. Hein et al., J. Amer. Chem. Soc., Vol. 79, p. 427 (1957).

The benzimidazolo-quinazolines, according to the invention, of the formula (I) are used as colour formers in pressure- and heat-sensitive recording materials. They are normally colourless or, at most, weakly coloured.

When these colour formers are brought into contact with a preferably acidic developer, i.e. an electron acceptor, intensive yellow to red colour tones are produced which have excellent fastnesses. They exhibit a good colour intensity, sublimation and light fastness on phenolic bases and, particularly, on activated clays as developers.

Typical examples of developers are inorganic substances such as clays, metal salts or oxides, phenols, phenolcarboxylic acids or esters thereof, or organic polymers such as phenol resins.

The compounds (I) may also be employed as a mixture with other known colour formers, for example 3,3-bis(aminophenyl)-phthalides, 3,3-bis-(indolyl)-phthalides, 3-aminofluorans, 2,6-diamino-fluorans, leucoauramines, spiropyrans, spirodipyrans, chromenoindoles, phenoxazines, phenothiazines, carbazolylmethanes or further triarylmethane leuco dyestuffs.

The compounds (I) are above all suitable as colour formers in a recording material which can be both copying and recording material. Their development speed differs, depending on the substituents. A low development speed leads to a reduced sensitivity of the recording material towards unintentional premature development.

In the thermoprinting process, in particular, print having extremely high fastnesses and high insensitivity towards the influence of both acid and basic media can be obtained using the colour formers according to the invention.

A pressure-sensitive material comprises, for example, at least one pair of sheets which contain at least one colour former of the formula (I), dissolved or dispersed in a non-volatile organic solvent, and an electron acceptor as developer.

The colour former provides a coloured mark at the points at which it comes into contact with the electron acceptor. In order to prevent premature activation of the colour former, these are generally separated from the electron acceptor. This can expediently be achieved by incorporating the colour former in foamy, spongy or honeycomb-like structures. The colour formers are preferably enclosed in microcapsules. Processes are known for the preparation of such microcapsules.

Suitable non-volatile solvents are, for example, partially hydrogenated terphenyl, alkylated naphthalenes or dibutyl phthalate.

The compounds of the formula (I) may preferably also be used as colour formers in a thermoreactive recording material. This generally contains at least one coating base, a colour former, an electron acceptor and, if appropriate, also a binder.

Thermoreactive recording systems cover, for example, heat-sensitive recording and copying materials and papers. These systems are used, for example, for recording information, for example in electronic computers, teleprinters, telex machines or in recording instruments and measuring instruments, such as, for example, electrocardiographs. The image generation (marking) can also be carried out manually using a heated nib. A further device for the generation of marks by means of heat are laser beams.

Suitable developers are the same electron acceptors as are used in pressure-sensitive papers, preferably phenolic compounds as are described, for example, in German Patent Specification No. 1,251,348, and also boric acid and organic, preferably aliphatic dicarboxylic acids.

Meltable, film-forming binders are preferably used for the preparation of the thermoreactive recording material. These binders are normally water-soluble, whereas the compounds (I) and the developers are sparingly soluble or insoluble in water.

The binder softens or melts under the influence of heat, so that the colour former comes into contact with the developer and a colour is able to form. Binders which are water-soluble or at least swellable in water are, for example, hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

The thermoreactive coatings may contain further additives: for improving the brightness, for simplifying the printing of the papers, for preventing adhesion of the heated nibs, and for forming colours only within a limited temperature range.

The processes and preparations described are known, for example, from U.S. Pats. Nos. 2,948,753, 3,096,189 and 3,193,404, and from German Published Specifications Nos. 2,555,080 and 2,700,937.

EXAMPLE 1

A mixture of 10.45 g of 2-(o-aminophenyl)-benzimidazole and 7.45 g of 4-dimethylaminobenzaldehyde is refluxed in 100 ml of ethanol. After 5 hours, the mixture is cooled and the precipitate is filtered off. 16.8 g of a compound of the formula

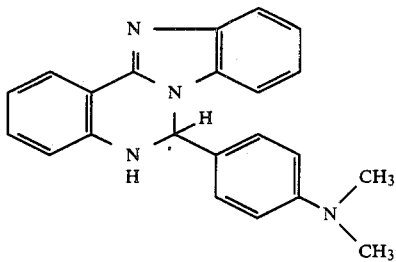

are obtained in the form of pale yellow coarse crystals having the melting point: 185° C.

This colour former develops an intensive yellow colour on acid clay.

The 2-(o-aminophenyl)-benzimidazole used above is obtained as follows: A mixture of 120 g of o-phenylenediamine and 165 g of ethyl salicylate is heated slowly to 230° C. in 1 kg of polyphosphoric acid (82.5% of $P_2O_5$). The reaction solution is kept at this temperature for 1 hour and then allowed to cool to 150° C., and the solution is discharged onto 2 kg of ice. The reaction product is filtered off under suction after the aqueous solution has been rendered weakly alkaline. After recrystallization from ethanol, a pale brown product of the formula

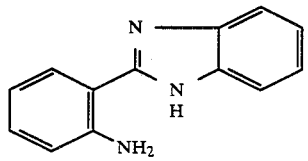

having the melting point 208° C. is produced.

EXAMPLE 2

A mixture of 20.9 g of 2-(o-aminophenyl)-benzimidazole and 23.1 g of 1,2,3,4-tetrahydro-1-ethyl-2,2,4-trimethylquinolin-6-aldehyde in 200 ml of ethanol is heated to reflux. After 5 hours, the solvent is removed on a rotary evaporator and the residue is triturated with a little methanol. 39.8 g of a virtually colourless powder of the formula

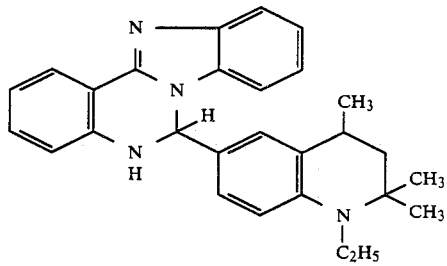

having the melting point 230° C. are obtained.

This colour former develops an intensive reddish yellow colour on acid clay.

EXAMPLE 3

If 20.9 g of 2-(o-aminophenyl)-benzimidazole and 18.8 g of 4-N-methyl-N-cyanoethyl-benzaldehyde are reacted by the process described in Example 2, 38.0 g of a solidified oil of the formula

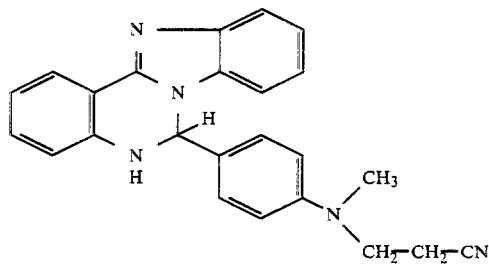

having the melting point 90° C. are obtained.

This colour former develops a neutral yellow colour on acid clay.

EXAMPLE 4

If 20.9 g of 2-(o-aminophenyl)-benzimidazole and 17.5 g of 4-dimethylamino-cinnam aldehyde are reacted with one another by the process described in Example 2, 34.5 g of a pale brown oil of the formula

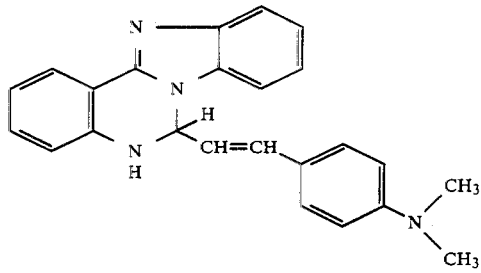

which solidifies at 121° C. are obtained after filtration through a silica gel column.

This colour former gives an intensive dull red colour on acid clay.

EXAMPLE 5

A solution of 34.0 g of the colour former from Example 1 in 60 ml of DMF is added, at a temperature of 50° C., with vigorous stirring to a suspension of 24.6 g of tetrachlorobenzoquinone in 150 ml of dimethylformamide. The end of the reaction is determined by thin layer chromatography. 29.0 g of virtually colourless crystals of the formula

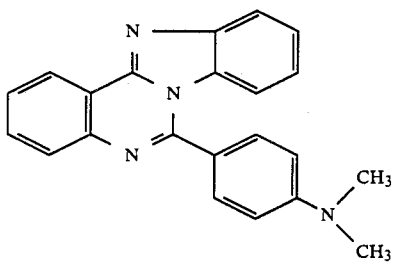

having the melting point 191° C. are obtained by discharging onto ice, filtering off under suction and recrystallizing from methanol.

This colour former develops an intensive yellow colour on acid clay.

EXAMPLE 6

A solution of 21.1 g of the colour former prepared in Example 2 is added, at 40° C., to a suspension of 12.3 g of tetrachlorobenzoquinone in 80 ml of dimethylformamide. After the completion of the oxidation (TLC check), the reaction mixture is discharged into ice water and filtered, and the brown residue is recrystallized from methanol with activated charcoal. 16.3 g of a pale yellow powder of the formula

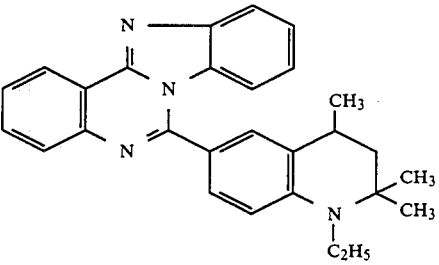

having the melting point 194° C. are isolated.

This colour former develops an intensive reddish yellow colour on acid clay.

The colour formers (a) and (b) may also be prepared according to Example 1, 2 or Example 5.

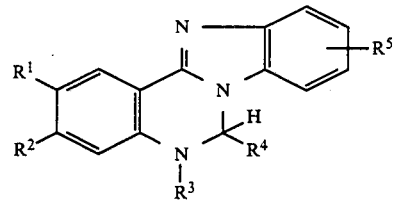

(a)

| Example | $R^1$ | $R^2$ | $R^3$ | $R^4$ | $R^5$ | Colour on acid clay |
|---|---|---|---|---|---|---|
| 7 | H |  | Cl | CH$_3$ | -C$_6$H$_4$-N(C$_2$H$_5$)(C$_2$H$_4$Cl) | OCH$_3$ | yellow |
| 8 | N(CH$_3$)$_2$ | H | H | -C$_6$H$_4$-N(C$_4$H$_9$)$_2$ | H | reddish yellow |
| 9 | H | H | H | -C$_6$H$_4$-N(CH$_3$)(C$_6$H$_5$) | CH$_3$ | yellow |
| 10 | H | H | H | N-ethylcarbazol-3-yl | H | yellow |
| 11 | H |  | Cl | C$_2$H$_5$ | 4-N(C$_2$H$_5$)$_2$-2-OC$_2$H$_5$-C$_6$H$_3$- | H | reddish yellow |

-continued

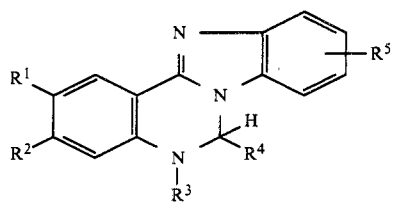

(a)

| Example | R¹ | R² | R³ | R⁴ | R⁵ | Colour on acid clay |
|---|---|---|---|---|---|---|
| 12 | H | H | H | 7-methyl-4-ethyl-3,4-dihydro-2H-benzo[b][1,4]oxazine | H | reddish yellow |
| 13 | H | Cl | H | N,N-dibenzyl-3-methyl-4-aminophenyl | H | yellow |
| 14 | H | H | H | 3-methylindol-2-yl | H | yellow |
| 15 | H | H | H | 1-ethyl-2,3-dimethylindol-5-yl | H | yellow |
| 16 | H | H | H | 1,2-dimethyl-5-methylindolin-6-yl | H | yellow |
| 17 | N(CH₃)₂ | H | H | 1-ethyl-2,3,3-trimethyl-5-methylindolin-6-yl | H | reddish yellow |
| 18 | H | H | H | 1-ethyl-2-phenyl-3-methylindol-5-yl | H | yellow |
| 19 | H | H | H | N,N-bis(2-acetoxyethyl)-3-methyl-4-aminophenyl | H | yellow |

-continued
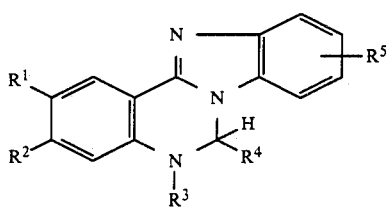
(a)
| Example | R¹ | R² | R³ | R⁴ | R⁵ | Colour on acid clay |
|---|---|---|---|---|---|---|
| 20 | H | Cl | H | 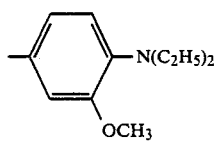 | H | reddish yellow |
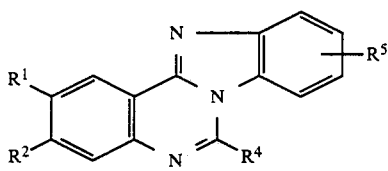
(b)
| Example | R¹ | R² | R⁴ | R⁵ | Colour |
|---|---|---|---|---|---|
| 21 | H | H | with N(C₂H₄Cl)(C₄H₉) | H | yellow |
| 22 | N(CH₃)₂ | H | with N(C₂H₅)(C₂H₄CN) | H | yellow |
| 23 | H | Cl | piperidinyl-phenyl | OCH₃ | yellow |
| 24 | H | H | morpholine-fused N-CH₃ | CH₃ | reddish yellow |
| 25 | H | H | N(CH₂-phenyl)₂ | H | yellow |
| 26 | H | H | with N-CH₃ and C(CH₃)₂-CH(CH₃)₂ | H | yellow |

-continued

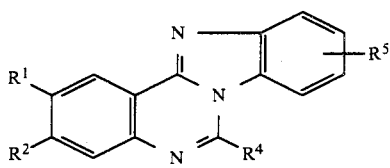
(b)

| Example | R¹ | R² | R⁴ | R⁵ | Colour |
|---------|-----|-----|-----|-----|--------|
| 27 | H | H | 3-methyl-1-methyl-indol-2-yl | Cl | yellow |
| 28 | H | H | 4-diethylamino-2-ethoxyphenyl | H | reddish yellow |
| 29 | N(CH₃)₂ | H | 9-ethylcarbazol-3-yl | H | reddish yellow |
| 30 | H | Cl | 4-[N-(2-cyanoethyl)-N-ethyl-amino]phenyl | H | yellow |
| 31 | H | H | 4-[N-ethyl-N-(2-ethoxycarbonyloxyethyl)amino]phenyl | H | yellow |

EXAMPLE 32

Preparation of a non-carbon copy paper (a.) Preparation of the microcapsule dispersion 10.0 g of the leuco compound, prepared according to Example 1, are dissolved in 161.1 g of a diisopropylated naphthalene with stirring and warming to 80° C., and, after cooling to room temperature, 36.75 g of oxadiazinetrionedi-hexamethylene diisocyanate (NCO content 21.0%) and 40.4 g of isohexadecane are added with stirring.

This organic solution is transferred into 385 g of a 0.5% strength, aqueous solution of a partly saponified polyvinyl acetate (degree of saponification 90%), and an emulsion having this droplet size of 6–8 μm is prepared in a mixing siren at 15,700 rpm. 6.1 g of diethylenetriamine, dissolved in 61.8 g of water, are added to this emulsion with stirring. The resultant 35% strength microcapsule dispersion is stirred for 20 minutes at 35° C. and, after heating, for 2 hours at 60° C. (b.) Preparation of the copy paper The microcapsule dispersion prepared in a.) is diluted with water to a capsule proportion of 15% by weight and brushed onto a base paper (50 g/m²) using a 30 ρm brush doctor.

The paper is dried, and a cover sheet of a noncarbon copy paper is thus prepared.

A sample of the copy paper is placed with the microcapsule-coated side on an acid clay-coated, commercially available acceptor paper (Giroset GF from the Feldmühle company), and 3 further papers are placed on top. This paper set is inscribed with the letter "w" using a typewriter. A true copy of the "w" in an intensive yellow colour becomes visible on the acceptor paper.

EXAMPLE 33

Preparation of a heat-sensitive recording sheet 3.6 g of an ester wax having a dripping point of 79°–85° C. (Hoechst Wax E from Hoechst AG), 41 g of kaolin, 18 g of a partly saponified polyvinyl alcohol (Mowiol 26–88 from Hoechst AG), 32 g of bis-(4-hydroxyphenyl)-dimethylmethane and 500 g of water are carefully ground in a ball mill until a particle size of about 10 μm is reached.

10.0 g of the leucodyestuff, which was prepared according to Example 2, 3 g of a partly saponified polyvinyl alcohol (Mowiol 26–88 from Hoechst AG) and 60 g of water are mixed thoroughly using an Ultra-Turrax mixer at 20,000 rpm until the dyestuff is finely distributed. The foam which forms during this is destroyed by several drops of tributyl phosphate.

The two dispersions are mixed with one another and brushed onto a base paper (50 g/m²) using a 30 μm brush doctor, and carefully dried. The coating weight is 5.0 g/m². If the coated paper is touched with a heated needle, an intensive yellow colour is produced.

Corresponding intensive, sublimation and lightfast yellow to red copies are also achieved by using each of the other colour formers specified in the Preparation Examples 2 to 31.

EXAMPLE 34

If the benzimidazoloquinazoline of Example 1 is replaced, in Example 32, by a mixture of the following composition:
1.4 g of 3,3-bis-(4'-dimethylaminophenyl)-6-dimethylaminophthalide,
1.0 g of N-butylcarbazol-3-yl-bis-(4'-N-methyl-N-phenylaminophenyl-)methane,
0.6 g of benzimidazoloquinazoline of Example 1 and
0.5 g of 3,3-bis-(N-n-octyl-2'-methylindol-3'-yl)phthalide,
and the process as described in Example 32 is otherwise followed, a pressure-sensitive recording material which produces an intensive and lightfast black copy by writing by hand or using a typewriter is obtained.

We claim:

1. A benzimidazolo-quinazoline of the formula

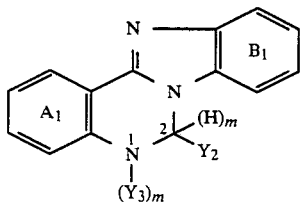

in which
$Y_2$ denotes a radical of the formula

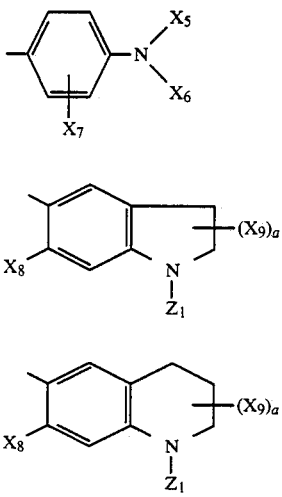

or

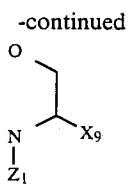

$Y_3$ denotes hydrogen or $C_1-C_4$-alkyl,
$X_5$ and $X_6$, independently of one another, denote $C_1-C_6$-alkyl which may be substituted by halogen, $C_1-C_4$-alkoxy or cyano, cyclopentyl or cyclohexyl, each of which may be substituted by 1-4 $C_1-C_4$-alkyl radicals, or denote phenyl, benzyl or phenethyl, each of which may be substituted by 1 or 2 $C_1-C_4$-alkyl, $C_1-C_4$-alkoxy, halogen, nitro, cyano or $C_1-C_4$-alkoxycarbonyl radicals, or $X_5$ and $X_6$, together with the nitrogen atom connecting them, denote a pyrrolidine, piperidine or morpholine radical which may be substituted by $C_1-C_4$-alkyl,
$X_7$ denotes hydrogen, halogen, $C_1-C_4$-alkyl, $C_1-C_4$-alkoxy or $C_1-C_4$-alkoxycarbonyl,
$X_8$ denotes hydrogen, halogen, $C_1-C_4$-alkyl or $C_1-C_4$-alkoxy,
$X_9$ denotes $C_1-C_4$-alkyl or phenyl, or 2 radicals $X_9$, which are both located on the same C atom, together denote trimethylene or tetramethylene,
a denotes 0 or 1-4, and
$Z_1$ denotes hydrogen, $C_1-C_8$-alkyl which may be substituted by halogen, cyano or $C_1-C_4$-alkoxy, benzyl or phenethyl, each of which may be substituted by halogen, $C_1-C_4$-alkyl or $C_1-C_4$-alkoxy,
m denotes 0 or 1,
in which a double bond is located between the positions labelled with 1 and 2 when m=0 and a single bond is between these positions when m=1, and in which the rings $A_1$ and $B_1$ may be substituted by one or two radicals selected from cyano, halogen, $C_1-C_4$-alkyl, $C_1-C_4$-alkoxy, $NX_5X_6$, phenyl or benzyl.

2. A benzimidazolo-quinazoline according to claim 1 of the formula

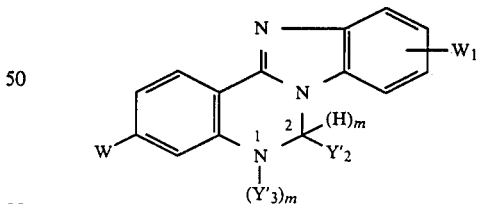

in which
W and $W_1$ denote hydrogen, chlorine, bromine, methyl or methoxy,
$Y'_2$ denotes a radical of the formulae

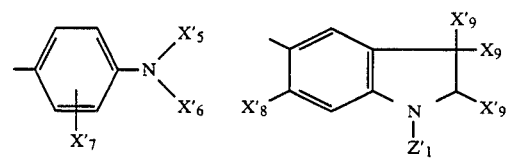

-continued

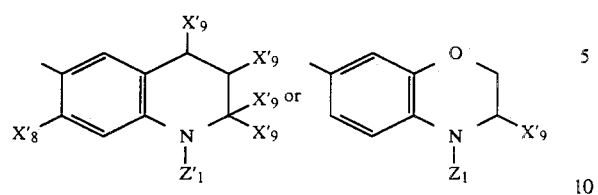

$Y'_3$ denotes hydrogen or methyl, $X'_5$ and $X'_6$, independently of one another, denote $C_1-C_6$-alkyl or benzyl, or —N $X'_5 X'_6$ denotes piperidino, $X'_7$ denotes hydrogen, methyl, methoxy or ethoxy, $X'_8$ denotes hydrogen or methyl, $X'_9$ denotes hydrogen, methyl or ethyl, and $Z'_1$ denotes $C_1-C_8$-alkyl, $\beta$-cyanoethyl or benzyl 3. A benzimidazolo-quinazoline according to claim 2 of the formula

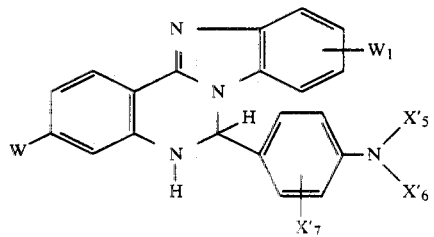

4. A benzimidazolo-quinazoline according to claim 2 of the formula

* * * * *